(12) United States Patent
Goto et al.

(10) Patent No.: US 7,964,554 B2
(45) Date of Patent: Jun. 21, 2011

(54) POLYPEPTIDE THAT BINDS ANTI-HISTONE H1 ANTIBODY

(75) Inventors: Takeshi Goto, Ushiku (JP); Shuji Sato, Narita (JP); Kazuhisa Ono, Higashi-Hiroshima (JP); Seiko Shigeta, Hiroshima-Ken (JP); Seiji Kawamoto, Higashi-Hiroshima (JP); Shigeru Goto, Oita-Ken (JP)

(73) Assignee: Amateraspharma Inc., Chiba-Ken (JP)

( * ) Notice: Subject to any disclaimer, the term of this patent is extended or adjusted under 35 U.S.C. 154(b) by 612 days.

(21) Appl. No.: 11/661,763

(22) PCT Filed: Sep. 5, 2005

(86) PCT No.: PCT/JP2005/016268
§ 371 (c)(1),
(2), (4) Date: Apr. 3, 2007

(87) PCT Pub. No.: WO2006/025580
PCT Pub. Date: Mar. 9, 2006

(65) Prior Publication Data
US 2008/0287352 A1    Nov. 20, 2008

(30) Foreign Application Priority Data
Sep. 3, 2004 (JP) .................................. 2004-257528

(51) Int. Cl.
*C07K 7/08* (2006.01)
*C07K 17/02* (2006.01)
(52) U.S. Cl. .......................................... 514/1; 530/327
(58) Field of Classification Search .................. None
See application file for complete search history.

(56) References Cited

U.S. PATENT DOCUMENTS
6,204,242 B1   3/2001   Bae et al.
2004/0052780 A1   3/2004   Ono et al.

FOREIGN PATENT DOCUMENTS
JP   2004-149507   5/2004
WO   99/37318   7/1999
WO   99/45955   9/1999

OTHER PUBLICATIONS

Schett et al., Arthritis and Rheumatism, 47(8):1446-1455, 1998.*
Chen et al., J. Gastroenterology and Hepatology, 13:483-489, 1998.*
Feng et al., Clinical Chemistry, 50(2):416-422, 2004.*
Nakano et al., Transplantation, 77(10):1595-1603, May 2004.*
Fournel et al., Current Protein and Peptide Science, 4(4): 261-276, 2003.*
Stemmer et al., Molecular Immunology, 31(14):1037-1046, 1994.*
Nakano et al., Transpl Immunol, 19(2):87-92, May 1, 2008.*
Supplementary European Search Report issued Apr. 14, 2010 in International (PCT) Application No. PCT/JP2005016268.
Gillissen, Guenther, "Immunosuppressive effect of histone in transplantation immunity. Comparative studies with cyclophosphamide", XP002574784, retrieved from STN Database Accession No. 1970:496837-Abstract. *Zeitschrift Fuer Die Gesamte Experimentelle Medizin, vol. 152, No. 4, 1970, pp. 335-351, ISSN: 0372-8722.
S. Dousson et al., "Histone H1° mapping using monoclonal antibodies", European Journal of Immunology, vol. 19, No. 6, Jun. 1989, pp. 1123-1129.
T. Nakano et al., "Liver Transplantation-Induced Antihistone H1 Autoantibodies Suppress Mixed Lymphocyte Reaction", Transplantation, vol. 77, No. 10, May 27, 2004, pp. 1595-1603.
N. Tuaillon et al., "Sequence analysis and fine specificity of two human monoclonal antibodies to histone H1", Molecular Immunology, vol. 31, No. 4, Mar. 1994, pp. 269-277.

* cited by examiner

*Primary Examiner* — Lorraine Spector
*Assistant Examiner* — Stacey MacFarlane
(74) *Attorney, Agent, or Firm* — Wenderoth, Lind & Ponack L.L.P.

(57) ABSTRACT

The present invention discloses anti-histone H1 monoclonal antibodies, hybridomas for the production thereof, and polypeptides, which are useful for suppressing, predicting, or diagnosing transplant rejection in organ transplantation.

4 Claims, 1 Drawing Sheet

POLYPEPTIDE THAT BINDS ANTI-HISTONE H1 ANTIBODY

This application is a U.S. national stage of International Application No. PCT/JP2005/016268 filed Sep. 5, 2005.

CROSS-REFERENCE TO RELATED APPLICATIONS

This application claims the benefit of priority from the prior Japanese Patent Application No. 2004-257528 filed on Sep. 3, 2004, the entire disclosure of which is incorporated herein by reference.

BACKGROUND OF THE INVENTION

1. Field of the Invention

The present invention relates to an anti-histone H1 monoclonal antibody, a hybridoma for the production thereof, and a polypeptide which the anti-histone H1 antibody specifically recognizes. More specifically, the present invention relates to a monoclonal antibody, a hybridoma producing thereof, and polypeptide, which are useful for suppressing, predicting, or diagnosing transplant rejection in organ transplantation.

2. Background Technology

In organ transplantation medicine, in order to suppress transplant rejection after organ transplantation, various immunosuppressive agents have so far been used. Examples of such immunosuppressive agents include tacrolimus (FK506) and cyclosporin A (Jpn J Pharmacol, 71, 89-100, 1996). However, conventional immunosuppressive agents have problems such as strong side effects including promotion of the growth of cancer cells and suppression of bone marrow functions, infections, and need for long-lasting administration (Transplantation, 58, 170-178, 1994).

Further, it is generally difficult to assess the time to withdraw immunosuppressive agents. For example, transplanted tissue occasionally survives without continuing the administration of an immunosuppressive agent. In such cases, if the administration of an immunosuppressive agent is carelessly continued, damages simply due to its toxicity may be done to a patient. On the other hand, it is also possible that surviving tissue becomes rejected by discontinuing the administration of an immunosuppressive agent. In this case, the rejection often cannot be evaded by restarting the administration of an immunosuppressive agent.

On the other hand, various studies on organ transplantation have been carried out. For example, in the system of orthotopic liver transplantation (OLT), it has been reported that when the liver of a donor DA rat (MHC haplotype, RT1a), which has a high graft survival rate, was transplanted into a recipient PVG rat (RT1c), the graft survived without administering an immunosuppressive agent (Transplantation, 35, 304-311, 1983).

Further, it has been reported that transplant graft rejection is suppressed in a transplantation model system related to a combination which generates transplant rejection by administering once prior to operation the serum of a recipient PVG rat into which the liver of DA rat was transplanted (post-OLT serum) to the system (J. Surg. Res., 80, 56-61, 1998).

Further, it has been disclosed that transplant rejection is suppressed and a recipient survives in a heart transplantation system of a DA rat (RT1a) and a LEWIS rat (RT1l) (in vivo), which always generates transplant rejection by administering an anti-histone H1 polyclonal antibody to the systemto after operation (Transplantation, 77, 1595-1603, 2004).

Further, some of the present inventors have disclosed that mixed lymphocyte reaction (MLR) is suppressed by using serum derived from a PVG rat in the early stage after transplantation and that an anti-histone H1 antibody has an MLR suppressive activity (Japanese Patent Laid-open Publication No. 2004-149507).

However, the development of a novel immunosuppressive agent which can suppress transplant rejection in organ transplantation and is excellent in safeness and its immunosuppressive activity still has been desired. Further, since it is necessary to monitor prognosis of patients or to prevent unnecessary administration of immunosuppressive agents in organ transplantation, the development of a novel drug with excellent accuracy for predicting or diagnosing the incidence of transplant rejection has also been desired.

SUMMARY OF THE INVENTION

The present inventors have now found an anti-histone H1 monoclonal antibody which has a marked immunosuppressive activity and is useful in suppressing, predicting, and diagnosing transplant rejection, and a hybridoma which produces this antibody. Further, the present inventors have found a specific amino acid sequence which is specifically recognized by the abovementioned anti-histone H1 monoclonal antibody. The present invention is based on these findings.

Accordingly, an objective of the present invention is to provide an anti-histone H1 monoclonal antibody which has a marked immunosuppressive activity and is useful in suppressing, predicting, or diagnosing transplant rejection and a hybridoma which produces this antibody.

Further, an objective of the present invention is to provide a polypeptide comprising a specific amino acid sequence which is specifically recognized by the abovementioned anti-histone H1 monoclonal antibody.

The monoclonal antibody according to the present invention recognizes histone H1 or a histone H1-like antigen present in the cell membrane of a spleen cell.

Further, the hybridoma according to the present invention produces the abovementioned monoclonal antibody.

Further, the polypeptide according to the present invention comprises a specific amino acid sequence which is recognized by the monoclonal antibody according to the present invention.

The monoclonal antibody according to the present invention has a marked immunosuppressive activity and safeness and can be advantageously used as an excellent immunosuppressive agent. Further, the monoclonal antibody according to the present invention has an excellent specificity to an autoantigenic protein in a mammal which makes an index of transplant rejection, so that it can be advantageously used for predicting or diagnosing transplant rejection in organ transplantation of a mammal.

Further, the polypeptide according to the present invention can be advantageously used as an immunosuppressive agent since it can induce the production of an anti-histone H1 antibody in the living body when used as an antigen. Furthermore, the polypeptide according to the present invention can be used for measuring the amount of anti-histone H1 antibody produced in a mammal, so that it can be advantageously used for predicting or diagnosing transplant rejection in organ transplantation.

DETAILED DESCRIPTION OF THE INVENTION

Deposition

Figure 1:
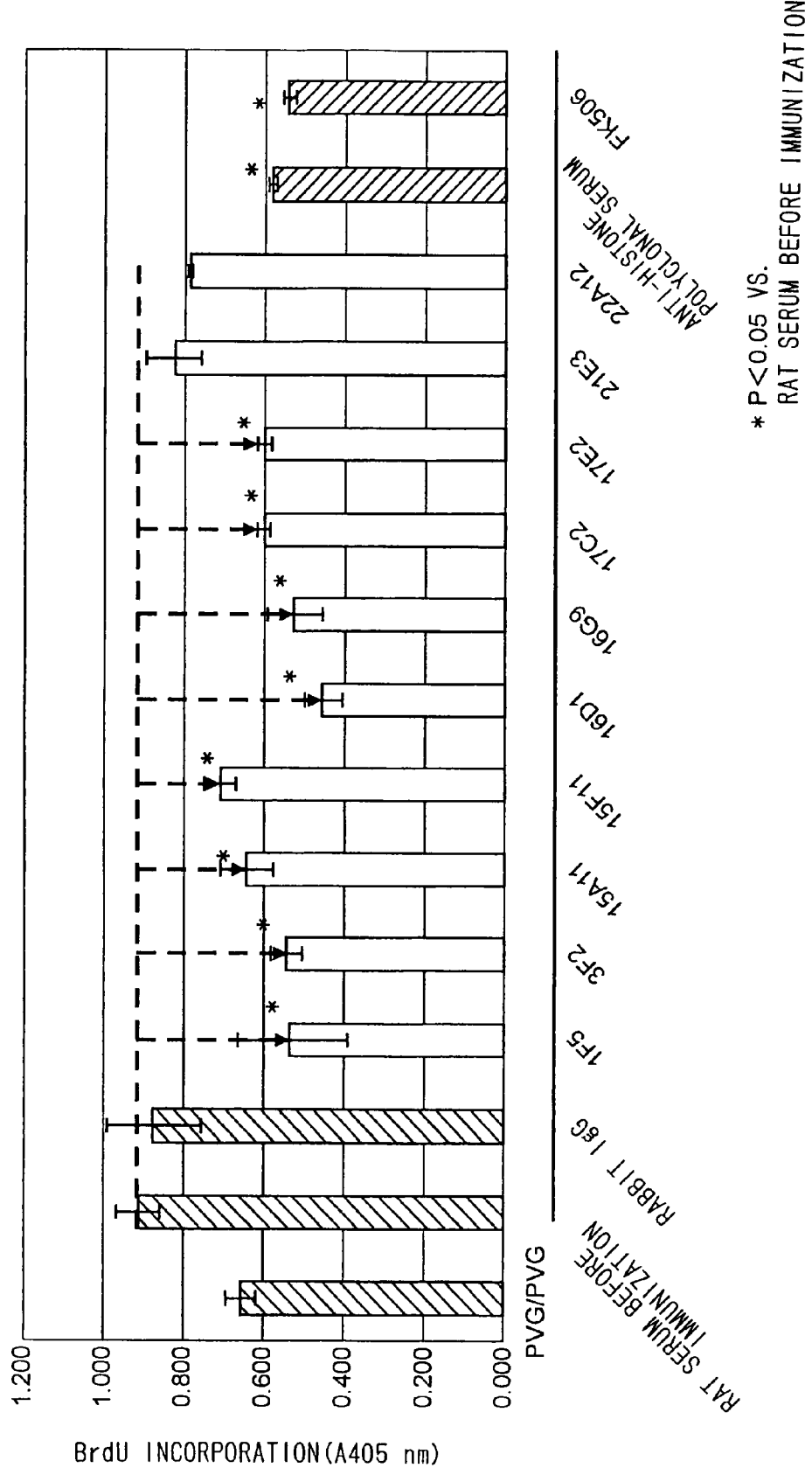
FIG. 1 shows the result of the evaluation for the MLR-suppressing activity using culture supernatants containing an anti-histone H1 monoclonal antibody.

The hybridomas according to the present invention, i.e., hybridoma 1F5, hybridoma 3F2, hybridoma 15F11, hybridoma 17C2, and hybridoma 16G9, have originally been deposited with the International Patent Organism Depositary, National Institute of Advanced Industrial Science and Technology (Central 6, 1-1-1 Higashi, Tsukuba, Ibaraki, Japan) on Aug. 19, 2004, under Accession Numbers FERM ABP-10409, FERM ABP-10410, FERM ABP-10411, FERM ABP-10412, and FERM ABP-10413, respectively.

Monoclonal Antibodies and Hybridomas

A monoclonal antibody according to the present invention recognizes histone H1 or a histone H1-like antigen present in a spleen cell. Further, the monoclonal antibody according to the present invention recognizes an epitope in an amino acid sequence preferably represented by SEQ ID NO: 4, SEQ ID NO: 5, SEQ ID NO: 6, SEQ ID NO: 7, or SEQ ID NO: 8. Further, according to another preferred embodiment of the present invention, the anti-histone H1 monoclonal antibody recognizes a polypeptide comprising an amino acid sequence represented by SEQ ID NO: 4, SEQ ID NO: 5, SEQ ID NO: 6, SEQ ID NO: 7, or SEQ ID NO: 8. Said polypeptide preferably consists of about 12-150 amino acid residues. Further, according to another preferred embodiment of the present invention, the anti-histone H1 monoclonal antibody recognizes a polypeptide consisting of an amino acid sequence represented by SEQ ID NO: 4, SEQ ID NO: 5, SEQ ID NO: 6, SEQ ID NO: 7, or SEQ ID NO: 8. Further, according to another preferred embodiment of the present invention, the anti-histone Hi monoclonal antibody is produced by one or more hybridomas selected from the group consisting of hybridoma 1F5, hybridoma 3F2, hybridoma 15F11, hybridoma 17C2, and hybridoma 16G9.

The term "histone H1" refers to a basic protein which is present in a eukaryotic cell and binds nucleosome linker DNA to form a nucleosome. Examples of such histone Hi include one which is derived from a human and comprises an amino acid sequence represented by SEQ ID NO: 1, one which is derived from cattle and comprises an amino acid sequence represented by SEQ ID NO: 2, and one which is derived from a mouse and comprises an amino acid sequence represented by SEQ ID NO: 3.

The term "histone H1-like antigen" refers to an antigen which is recognized by a monoclonal antibody produced by hybridoma 1F5, hybridoma 3F2, hybridoma 15F11, hybridoma 17C2, or hybridoma 16G9 in the cell membrane of a spleen cell. This histone H1-like antigen preferably constitutes a part of a protein having a molecular weight of 31 kD on SDS-PAGE. An example of such histone H1-like antigen is a protein having at least a part of the amino acid sequence of histone H1 derived from a mammal.

Further, the monoclonal antibody according to the present invention may be a chimeric antibody, a humanized antibody, or a complete humanized antibody, if desired. More specific examples include a chimeric antibody in which an antigen binding domain Fv of a mouse monoclonal antibody is alternatively introduced into a human antibody (Morrison, S. L., Oi, V. T., "Immunoglobulin Genes" Academic Press (London), 260-274 (1989)) and a humanized antibody in which a complementary determining region (CDR) that is a sequence on an Fv domain directly involved in the antigen binding of a mouse monoclonal antibody is embedded into a human antibody frame using CDR graft technology (Roguska, M. L. et. al., Humanization of murine monoclonal antibodies through variable domain resurfacing, Proc. Natl. Acad. Sci. USA, 91, 969-973 (1994)). Further, examples of the complete humanized antibody include one produced by the TransChromo Mouse to which a human antibody gene is transplanted (Tomizuka, K. et. al., Functional expression and germline transmission of a human chromosome fragment in chimaeric mice, Nature Genet., 16, 133-143 (1997)), or one produced by human antibody phage libraries (Winter, G. et. al., Making antibodies by phage display technology, Ann. Rev. Immunol., 12, 433-455 (1994); Griffiths, A. D. et. al., Isolation of high affinity human antibodies directly from large synthetic repertoires, EMBO. J., 13, 3245-3260 (1994)).

Further, according to another embodiment of the present invention, there is provided hybridoma 1F5, hybridoma 3F2, hybridoma 15F11, hybridoma 17C2, and hybridoma 16G9.

The monoclonal antibody and hybridoma according to the present invention can be manufactured, for example, as follows. Namely, first, the hybridoma according to the present invention can be obtained by using histone H1 or a histone H1-like antigen or a polypeptide containing an epitope thereof as a sensitizing antigen, fusing a mammalian plasma cell of a mammal immunized with this sensitizing antigen (immunocyte), with a mammalian myeloma cell, cloning the obtained hybridomas and selecting desired hybridomas from them. The monoclonal antibody according to the present invention can be obtained by culturing the hybridoma according to the present invention so as to recover the antibody produced by it.

The polypeptide containing histone H1 or a histone H1-like antigen or an epitope thereof used as sensitizing antigen can be derived, for example, from human leukemic bone marrow cells, human cervix uteri cancer Hela cells, bovine thymus gland, bovine liver, bird erythrocytes, and the like. This sensitizing antigen is suspended, for example, in PBS or physiological saline, and the suspension is used for immunization of a mammal with an adjuvant such as FCA (Freund's complete adjuvant) and KLH (keyhole limpet hemocyanin), if desired.

As a method of immunizing a mammal, a general administration method in this field of technology can be used. Specific examples of the administration method include intraperitoneal injection, intrasplenic injection intramuscular injection, subcutaneous injection, intracutaneous injection, oral administration, mucosal administration, and intradermal administration, preferably intraperitoneal injection and intrasplenic injection. The interval between administrations of the sensitizing antigen is appropriately determined depending on the dose of the sensitizing antigen, the kind of the mammal, and the like; for example, it can be administered several times a month.

The mammals to be immunized are not particularly limited; however, they are preferably selected taking into consideration compatibility with the myeloma cell used in cell fusion; examples include mice, rats, and hamsters, preferably mice.

Further, spleen cells are preferably used as immunizing cells.

Examples of the myeloma cell used in the present invention include P3 (P3X63Ag8.653) (J. Immunol., 123, 1548, 1978), p3-U1 (Current Topics in Microbiology and Immunology, 81, 1-7, 1978), NS-1 (Eur. J. Immunol., 6, 511-519, 1976), MPC-11 (Cell, 8, 405-415, 1976), Sp2/0-Ag14 (Nature, 276, 269-270, 1978), FO (J. Immunol. Meth., 35, 1-21, 1980), S194 (I. Exp. Med., 148, 313-323, 1978), and R210 (Nature, 277, 131-133, 1979), preferably P3 or p3-U1, and more preferably P3.

The cell fusion between an immunizing cell and a myeloma cell can be carried out, for example, according to the method of Milstein et al. (Methods Enzymol., 73, 3-46, 1981). More specifically, the cell fusion can be carried out, for example, by mixing the immunizing cell and the myeloma cell in a medium in the presence of a fusion promoting agent. In cell fusion, hybridomas can be produced by appropriately repeating the addition of medium and centrifugation.

The medium for cell fusion can be, for example, a medium generally used for cell fusion, such as RPMI-1640 medium and MEM medium. Further, serum supplements such as fetal bovine serum (FBS) can be appropriately used together.

Further, the cell fusion is carried out preferably at 25-37° C., more preferably at 30-37° C.

The mixing ratio of the myeloma cell and the immunizing cell is preferably about 1:1-1:10.

Examples of the fusion promoting agent include polyethylene glycol (PEG) and Sendai virus (HVJ), preferably PEG. The molecular weight of PEG can be appropriately selected; for example, the average molecular weight of PEG can be about 1,000 to 6,000. Further, the concentration of PEG in a medium is preferably about 30-60% (W/V).

Furthermore, if necessary, an auxiliary agent such as dimethyl sulfoxide is appropriately added to a medium.

Selection of a hybridoma according to the present invention can be carried out by culturing hybridomas obtained by cell fusion in a normal selective medium such as an HAT medium and performing screening by a general limiting dilution method, for example, using antibody titer to histone H1 as an index. The time for cultivation in the HAT medium is enough to kill cells (non-fused cells) other than a target hybridoma and can generally be several days to several weeks. A hybridoma according to the present invention thus obtained can be subcultured in a normal medium and stored in liquid nitrogen for a long period of time.

Further, examples of the method of recovering a monoclonal antibody according to the present invention include a method in which hybridomas are cultured by a normal method to obtain a monoclonal antibody from the resulting culture supernatant and a method in which hybridomas are administered to a compatible mammal for proliferation to obtain a monoclonal antibody from abdominal fluid of this mammal. The former method is preferred to obtain an antibody with a high purity, while the latter is preferred to produce an antibody in large quantities.

Furthermore, the monoclonal antibody according to the present invention can be purified to high purity using a salting-out method, a gel filtration method, affinity chromatography, and the like.

The monoclonal antibody according to the present invention has a marked immunosuppressive activity as mentioned above. The monoclonal antibody according to the present invention can be used as it is as an immunosuppressive agent; however, it can also be used as a pharmaceutical composition, particularly as a composition for suppressing immunity, along with pharmaceutically acceptable carriers and the like. Therefore, according to an embodiment of the present invention, there is provided a composition for suppressing immunity comprising the monoclonal antibody according to the present invention as active ingredient. According to another embodiment of the present invention, there is also provided use of the monoclonal antibody according to the present invention in manufacturing the composition for suppressing immunity.

The composition for suppressing immunity according to the present invention is useful for the treatment and prevention of transplant rejection in the transplantation of organs such as the heart, kidney, liver, bone marrow, and skin, further for the treatment and prevention of autoimmune diseases. The composition for suppressing immunity according to the present invention can be prepared, for example, by dissolving the monoclonal antibody according to the present invention in physiological saline for injection, distilled water for injection, a buffer solution for injection, and the like. Further, the composition for suppressing immunity according to the present invention can contain appropriate solvents, solubilizing agents, preservatives, stabilizers, emulsifiers, suspending agents, analgesic agents, isotonizing agents, buffering agents, fillers, thickening agents, coloring agents, and known carriers (e.g., various liposomes, polyamino acid carriers, synthetic polymers, natural polymers).

The composition for suppressing immunity according to the present invention can be administered either systemically or locally. Specific examples of the method of administration include dripping, intravenous injection, intramuscular injection, subcutaneous injection, intradermal injection, oral administration, mucosal administration, and transdermal administration. Therefore, according to another embodiment of the present invention, there is provided a method for treating a mammal which requires immunosuppression, comprising the administering a therapeutically effective amount of a monoclonal antibody according to the present invention to a mammal. The dose of the monoclonal antibody according to the present invention depends on the condition and age of the mammal and the like; however, generally, it can be administered a dose of 0.05-40 mg/kg bodyweight/day, preferably 0.1-1.0 mg/kg bodyweight/day in a single or several divided doses. Further, the administration can be a single or, for example, repeated over the period of 4 weeks.

Further, the monoclonal antibody according to the present invention can be used in predicting or diagnosing transplant rejection in a mammal since it specifically reacts with an auto-antigenic protein which is an index for transplant rejection upon organ transplantation. The auto-antigenic protein herein means a protein which is present in the mammal and preferably recognized by a monoclonal antibody produced by hybridoma 1F5, hybridoma 3F2, hybridoma 15F11, hybridoma 17C2, or hybridoma 16G9. Therefore, according to another embodiment of the present invention, there is provided a composition for predicting or diagnosing transplant rejection in a mammal, comprising the monoclonal antibody according to the present invention as active ingredient. To the abovementioned composition, pharmaceutically acceptable carriers can be added, if desired. Further, the abovementioned transplant rejection is preferably one which occurs after organ transplantation, more preferably one which occurs after withdrawal of the administration of an immunosuppressive agent. Further, according to another embodiment of the present invention, there is provided use of the monoclonal antibody according to the present invention as an agent for predicting or diagnosing transplant rejection in a mammal. Further, according to another embodiment of the present invention, there is provided a method for predicting or diagnosing transplant rejection in a mammal, comprising the measuring the level of immunoreactivity between a biological sample derived from a mammal and the monoclonal antibody according to the present invention. In the abovementioned method, the risk of transplant rejection is predicted or diagnosed to be high when the measured level of immunoreactivity is higher than a threshold value which is previously set referring to the level of immunoreactivity between a biological sample of a mammal suffering from transplant rejection and the monoclonal antibody according to the present invention. This threshold value is appropriately determined by those skilled in the art according to the species and sex of the mammal and a donor, the kind of transplant organ, the measuring method, and the like. According to the method for the prediction and the diagnosis according to the present invention, physical and financial burdens on a patient can be reduced by avoiding the administration of unnecessary immunosuppressive agents.

Further, an example of the abovementioned biological sample is preferably blood, more preferably serum.

The abovementioned immunosuppressive agents are not particularly limited as long as they are immunosuppressive agents used in organ transplantation. They can be alkylating agents such as cyclophosphamide; anti-metabolites such as azathiopurine, methotrexate, and mizoribine; T-cell activity inhibitors such as cyclosporin and tacrolimus; steroidal agents such as prednisolone, methylprednisolone, mycophenolate mofetil, and azathiopurine; and lymphocyte surface function inhibitors such as basiliximab and muromonab, or combinations thereof.

The abovementioned mammal and transplant organ donor can be, for example, humans, pigs, and baboons, preferably humans. Examples of the organ to be transplanted are the liver, heart, kidney, and skin.

A method of measuring the abovementioned level of immunoreactivity is not particularly limited as long as it utilizes antigen-antibody reaction; specific examples of the method include the fluorescence antibody method, the chemical staining method, the enzyme-antibody method, the ELISA method, radioimmunoassay, immunoprecipitation, the Western blot method, modified Western blot methods (e.g., the Western method, the Southwestern method, the Northwestern method, and West-western method), and the protein chip method. Therefore, according to another preferred embodiment of the present invention, the abovementioned level of immunoreactivity is measured by the fluorescence antibody method, the chemical staining method, the enzyme-antibody method, the ELISA method, radioimmunoassay, the immunoprecipitation method, the Western blot method, a modified Western blot method, or the protein chip method.

Further, according to another embodiment of the present invention, there is provided a kit for predicting or diagnosing transplant rejection in a mammal, comprising at least an anti-histone H1 monoclonal antibody. The abovementioned transplant rejection is preferably one which occurs after organ transplantation, more preferably one which occurs after withdrawal of the administration of an immunosuppressive agent.

Polypeptides

A polypeptide according to the present invention comprises the abovementioned epitope which is recognized by the anti-histone H1 monoclonal antibody according to the present invention, in its amino acid sequence. Further, according to a preferred embodiment of the present invention, the polypeptide consists of an amino acid sequence represented by SEQ ID NO: 4, SEQ ID NO: 5, SEQ ID NO: 6, SEQ ID NO: 7, or SEQ ID NO: 8.

Also, according to another preferred embodiment of the present invention, the polypeptide consists of a modified amino acid sequence which includes substitutions, deletions, or addition of one or several amino acids in an amino acid sequence represented by SEQ ID NO: 4, SEQ ID NO: 5, SEQ ID NO: 6, SEQ ID NO: 7, or SEQ ID NO: 8. As used herein, "one or several" generally ranges preferably about from 1 to 3, more preferably about from 1 to 2.

Further, according to another preferred embodiment of the present invention, the polypeptide consists of a partial sequence of an amino acid sequence represented by SEQ ID NO: 4, SEQ ID NO: 5, SEQ ID NO: 6, SEQ ID NO: 7, or SEQ ID NO: 8. Examples of the abovementioned partial sequence preferably include the partial sequence represented by amino acid number 6 to 9 in SEQ ID NO: 4, the partial sequence represented by amino acid number 5 to 9 in SEQ ID NO: 5, the partial sequence represented by amino acid number 2 to 5 in SEQ ID NO: 6, the partial sequence represented by amino acid number 2 to 5 in SEQ ID NO: 7, and the partial sequence represented by amino acid number 7 to 9 or amino acid number 11 to 12 in SEQ ID NO: 8.

Further, according to another embodiment of the present invention, the polypeptide comprises an amino acid sequence represented by SEQ ID NO: 4, SEQ ID NO: 5, SEQ ID NO: 6, SEQ ID NO: 7, or SEQ ID NO: 8, or a partial sequence thereof. Further, this polypeptide consists of preferably about 3 to 300, more preferably about 12 to 150 amino acid residues.

The amino acid sequence of the polypeptide according to the present invention is determined based on the analysis using a phage display peptide library kit with the monoclonal antibody according to the present invention. The polypeptide according to the present invention can be synthesized based on this amino acid sequence using a known peptide synthesizing device and the like.

Further, the polypeptide according to the present invention can be used for inducing the production of an anti-histone H1 antibody in the body, as is or after derivertizing it by a known method. Further, histone H1 or a histone H1-like antigen can also exhibit an immunosuppressive activity by administering it to the body as a sensitizing antigen to produce an anti-histone H1 antibody. Therefore, according to a preferred embodiment of the present invention, there is provided a composition for suppressing immunity comprising histone H1, a histone H1-like antigen, or a polypeptide according to the present invention as active ingredient. Further, according to another embodiment of the present invention, there is provided use of histone H1, a histone H1-like antigen, or a polypeptide according to the present invention in manufacturing the composition for suppressing immunity.

The abovementioned composition for suppressing immunity can be manufactured in a dosage form suited to its administration method along with pharmaceutically acceptable carriers. For example, when its dosage form is a fluid, appropriate solvents, solubilizing agents, preservatives, stabilizers, emulsifiers, suspending agents, analgesic agents, isotonizing agents, buffering agents, fillers, thickening agents, coloring agents, known carriers (e.g., various liposomes, polyamino acids, carriers, synthetic polymers, natural polymers), adjuvants, and the like can be appropriately contained.

A method for administrating the abovementioned composition for suppressing immunity can be any method usable in this field of technology, including intra-arterial injection, dripping, intravenous injection, intramuscular injection, subcutaneous injection, intradermal injection, oral administration, mucosal administration, and transdermal administration. Therefore, according to another embodiment of the present invention, there is provided a method for treating a mammal which requires immunosuppression, comprising administering a therapeutically effective amount of histone H1, a histone H1-like antigen, or a polypeptide according to the present invention, to a mammal. The therapeutically effective amount varies depending on the severity of the symptoms, sex, age, bodyweight, behavior of the mammal; however, the amount of the active ingredient can be 0.005 µg to 2 g/kg bodyweight/day. Further, its medication regimen can be appropriately made by those skilled in the art by confirming antibody production in the mammal.

Further, histone H1, a histone H1-like antigen, or a polypeptide according to the present invention can be used in measuring the amount of anti-histone H1 antibody in a mammal since it specifically reacts with an anti-histone H1 antibody produced in the mammal. Therefore, according to another embodiment of the present invention, there is provided a composition for measuring the amount of anti-histone H1 antibody in a biological sample derived from a mammal, comprising histone H1, a histone H1-like antigen, or a polypeptide according to the present invention as active ingredient. Since the abovementioned anti-histone H1 antibody has a function to suppress transplant rejection as mentioned above, the amount of anti-histone H1 antibody in the mammal makes an index for the prediction and diagnosis of transplant rejection. Therefore, according to another preferred embodiment of the present invention, the abovementioned composition can be used for the prediction and diagnosis of transplant rejection in a mammal. Further, according to another embodiment of the present invention, there is provided use of histone H1 according to the present invention, a histone H1-like antigen, or a polypeptide according to the present invention as agent for predicting or diagnosing transplant rejection in a mammal. The abovementioned transplant rejection is one which occurs after organ transplantation, more preferably one which occurs after withdrawal of the administration of an immunosuppressive agent. Further, according to another embodiment of the present invention, there is provided a method for predicting or diagnosing transplant rejection in a mammal, comprising measuring the level of immunoreactivity between an anti-histone H1 antibody in a biological sample in a mammal and histone H1, a histone H1-like antigen, or a polypeptide according to the present invention. In the abovementioned method, the risk of transplant rejection is predicted or diagnosed to be low when the measured level of immunoreactivity is higher than a threshold value which is previously set referring to the level of immunoreactivity between the anti-histone H1 antibody of a biological sample from a mammal suffering from transplant rejection and histone H1, a histone H1-like antigen, or a polypeptide according to the present invention. This threshold value is appropriately determined by those skilled in the art according to the species and sex of the mammal and a donor, the kind of transplant organ, the measuring method, and the like. According to the method of the prediction or diagnosis according to the present invention, physical and financial burdens on a patient can be reduced by avoiding the administration of unnecessary immunosuppressive agents.

A method for measuring the abovementioned level of immunoreactivity is not particularly limited as long as it uses the antigen-antibody reaction; specific examples of the method include the fluorescence antibody method, the chemical staining method, the enzyme-antibody method, the ELISA method, radioimmunoassay, immunoprecipitation, the Western blot method, or modified Western blot methods (e.g., the Western method, the Southwestern method, the Northwestern method, the West-western method), and the protein chip method. The abovementioned immunoreactivity level can be measured preferably by the fluorescence antibody method, the chemical staining method, the enzyme-antibody method, the ELISA method, radioimmunoassay, the immunoprecipitation method, the Western blot method, a modified Western blot method, or the protein chip method, more preferably the protein chip method. In the protein chip method, the prediction or diagnosis of transplant rejection in a mammal can be carried out rapidly and accurately by loading a polypeptide according to the present invention onto a protein chip.

Further, according to another embodiment of the present invention, there is provided a kit for measuring the amount of anti-histone H1 antibody in a biological sample derived from a mammal, comprising at least histone H1, a histone H1-like antigen, or a polypeptide according to the present invention. Further, according to another preferred embodiment of the present invention, the abovementioned kit is for predicting or diagnosing transplant rejection in a mammal. The abovementioned transplant rejection is preferably one which occurs after organ transplantation, more preferably one which occurs after withdrawal of the administration of an immunosuppressive agent.

The abovementioned biological samples, immunosuppressive agents, transplant organs, mammals, transplant organ donors, and the like are the same as in the therapeutic method and the method of predicting or diagnosing transplant rejection using the monoclonal antibody according to the present invention.

EXAMPLES

The following examples will specifically explain the present invention; however, they are not to be construed to limit the scope of the invention.

Reagents and antibodies used were of analytical grade, unless otherwise mentioned. Further, DA rats and PVG rats (males, 7 to 8 weeks of age) were purchased from Japan SLC, Inc and Seac Yoshitomi, Ltd., respectively. BALB/c mice (males, 5 to 6 weeks of age) were purchased from Charles River Japan, Inc.

Reference Example 1

Mixed lymphocyte reaction (MLR): Rat cells Splenic lymphocytes derived from untreated PVG rats (responding cells) and splenic lymphocytes derived from DA rats treated with mitomycine C (Kyowa Hakko Kogyo Co., Ltd.) (stimulating cells) were used. The responding cells were adjusted to $5 \times 10^5$ cells/mL with a 10% FCS-RPMI medium, and the stimulating cells were adjusted to $8 \times 10^6$ cells/mL with a 10% FCS-RPMI medium. The responding cell suspension and the stimulating cell suspension thus prepared were seeded each in a 100 ∥L portion onto a 96-well round bottom plate (Nunc Brand Products), after which at the start of mixed cultivation, anti-histone H1 polyclonal IgG (Santa Cruz Biotechnology, at 0.1, 0.2, 0.4, 0.8, or 1.6 μg/well) or rabbit IgG (normal rabbit IgG, Santa Cruz Biotechnology, at 0.1, 0.2, 0.4, 0.8, or 1.6 μg/well) were added and cultivation was carried out at 37° C. in an atmosphere of 5% $CO_2$/95% air for more than 3.5 days. Here, tacrolimus (FK506, Fujisawa Pharmaceutical Co., Ltd.) was added as a positive control. Further, 15 hours prior to completion of the cultivation, 10 μL of bromodeoxyuridine (BrdU) was added. Then, using a BrdU labeling & detection kit III (Roche Diagnostics), the degree of cell proliferation was determined using the amount of BrdU incorporated into intracellular DNA as an index. Here, the higher the degree of cell proliferation, the more BrdU is incorporated.

As a result, when anti-histone H1 polyclonal IgG was added, MLR was significantly inhibited and the inhibition level was the same as that of the case that tacrolimus was added.

Reference Example 2

Mixed Lymphocyte Reaction (MLR): Human Cells
Preparation of Lymphocytes

From two humans (A and B), 10 mL each of peripheral blood was taken and centrifuged (1500 rpm, 30 minutes), after which the plasma was removed. Next, PBS in the same volume as the removed plasma (3 mL) was added to the residue and the admixture was stirred. To this admixture, 3 ml of Ficoll-paque solution (Amersham Biosciences) was added and the resulting admixture was subjected to density gradient centrifugation (1500 rpm, 30 minutes) to obtain a white middle layer containing lymphocytes. The total volume of 12 mL of cell suspension was made by adding sterilized PBS to this white layer and subjected to centrifugation (1500 rpm, 5 minutes). After repeating this procedure twice, the lymphocytes obtained were suspended in 1 mL of 10% FCS-AIM-V medium (GIBCO).

MLR

The following test was carried out using lymphocytes derived from B (responding cells) and lymphocytes derived from A treated with mitomycin C (Kyowa Hakko Kogyo, Co., Ltd.) (stimulating cells). The responding cells were adjusted to $5 \times 10^5$ cells/mL with a 10% FCS-AIM-V medium, and the stimulating cells were adjusted to $8 \times 10^6$ cells/mL with a 10% FCS-RPMI medium. The responding cell suspension and the stimulating cell suspension thus prepared were seeded each in a 100 μl portion onto a 96-well round bottom plate (Nunc Brand Products), after which at the start of mixed cultivation, anti-histone H1 polyclonal IgG (Santa Cruz Biotechnology, at 0.1, 0.2, 0.4, 0.8, or 1.6 μg/well) or rabbit IgG (normal rabbit IgG, Santa Cruz Biotechnology, at 0.1, 0.2, 0.4, 0.8, or 1.6 μg/well) was added and cultivation was carried out at 37° C. in an atmosphere of 5% $CO_2$/95% air for 2.5 days. Here, tacrolimus was added as a positive control. Further, during cultivation, ConA was added to each well at a final concentration of 10 μl/mL to confirm that the proliferation of the stimulating cells was stopped and that the responding cells were proliferated by antigen stimulation. Then, each well was treated in the same manner as in Reference Example 1, and using a BrdU labeling & detection kit III (Roche Diagnostics), the degree of cell proliferation was determined using the amount of bromodeoxyuridine (BrdU) incorporated into intracellular DNA as an index.

In the combination of the responding cells derived from B and the stimulating cells derived from A treated with mitomycin C, cell proliferation by MLR was confirmed. Further, MLR was suppressed concentration-dependently by the anti-histone polyclonal antibody. On the other hand, MLR was not suppressed by rabbit IgG (normal rabbit IgG).

Example 1

Preparation of Hybridomas
Immunization

A suspension (antigen concentration: 0.25 mg/ml) was obtained by mixing 0.8 mL of a solution of an antigen (Histone H1 Histone F1 Histone KAP, Roche) in PBS (antigen concentration: 0.5 mg/mL) and 0.8 mL of Freund's complete adjuvant (Wako Pure Chemical Industries). Next, 0.2 mL of this suspension was intraperitoneally administered to a BALB/c mouse. Further, an equal amount of this suspension was administered to the mouse every 2 weeks. Then, 16 weeks after the start of administration, 0.2 mL of an antigen solution in PBS (antigen concentration: 600 to 1000 mg/mL) was lastly administered intraperitoneally to the mouse. Upon administration, blood was collected from the ocular fundus vein and the antibody titer was measured by ELISA. Four days after the final administration, whole blood was collected and the blood obtained was centrifuged (2000 rpm, 20 minutes) to obtain antiserum which was used as a control antiserum in the following experiment. Further, after whole blood was collected, the spleen was dissected from a rat and spleen cells obtained were used in the following cell fusion.

Cell Fusion

The abovementioned spleen cells and myeloma cells (P3X63-Ag.8.653) were mixed at a ratio of 10:1 to 10 and the mixture was centrifuged (1500 rpm, 5 minutes). After centrifugation, the supernatant was removed using an aspirator and to the resulting cell pellet, 1 mL of polyethylene glycol 4000 (50% solution in PBS) at 37° C. was added over a period of one minute to make a mixed solution. This mixed solution was allowed to stand at 37° C. for one minute, after which an IMDM medium (total 9 ml) at 37° C. was added at a rate of 1 mL per 30 seconds and then the admixture was centrifuged (1500 rpm, 5 minutes). After centrifugation, the supernatant was removed by suction and an appropriate amount of an IMDM medium (GIBCO) supplemented with 15% FCS (JRH BIOSCIENCES) at 37° C. was added. A 100 mL aliquot of the resulting suspension was each dispensed onto a 96 well culture plate and the plate was incubated at 37° C. for one day in a 50% $CO_2$ incubator. Further, 100 mL of an HAT medium (which was prepared by dissolving HAT powder (HAT MEDIA SUPPLEMENT (×50, Sigma) in 10 mL of a serum-free IMDM medium and diluting the solution 50 times with an IMDM medium containing 10% FCS) was added and incubation was carried out at 37° C. in a 5% $CO_2$ incubator. The HAT medium was changed every 2 to 3 days. After 10 days, the medium was changed to an HT medium (which was prepared by dissolving HT powder (HT MEDIA SUPPLEMENT, Sigma) in 10 mL of a serum-free IMDM medium and diluting the solution 50 times with an IMDM medium containing 10% FCS) and incubation was carried out at 37° C. for 3 days in a 5% $CO_2$ incubator. Then, the medium (HT medium) was changed every 2 to 3 days. After confirming cell proliferation under a microscope, the culture supernatant (about 100 mL) was recovered. Using this culture supernatant, hybridoma screening was carried out by measuring the antibody titer against histone H1 as shown below.

Screening of Hybridoma Cells
Measurement of Antibody Titer

An aliquot of 50 μL per well of a buffer solution containing histone H1 (5 mg, calf thymus histone H1, Roche Diagnostics) (bicarbonate buffer: 100 mM $NaHCO_3$—NaOH, pH 9.2-9.5; histone H1 concentration: 1 mg/mL) was dispensed onto a 96-well flat bottom plate and the plate was allowed to stand at room temperature for 2 hours for coating. The plate was washed 3 times with a washing buffer solution (PBST), a blocking buffer solution (3% skim milk and 1% BSA in PBS) was added at 200 to 250 μL/well, and after reacting at 4° C. for 24 hours, the plate was washed 3 times. Next, a 100 μL aliquot per well of the hybridoma culture supernatant was added and the reaction was carried out at 37° C. for 4 hours or at 4° C. for 24 hours. After washing the plate 3 times, a 50 μL aliquot per well of biotin-labeled anti-mouse IgG (Sigma) which was diluted 10000 times with a dilution buffer solution (10 mM Tris-HCl (pH 8.0), 0.9% (W/V) NaCl, 0.05% (W/V) Tween 20) was added and the reaction was carried out at room temperature for 2 hours. After washing 6 times, a 50 μL aliquot per well of alkaline phosphatase-labeled streptavidin which was diluted 1000 times with a dilution buffer was added and the reaction was carried out at room temperature for 1 to 2 hours. After washing 6 times, a 50 μL aliquot per well of a fluorescent substrate buffer (Attophos substrate buffer, Roche Diagnostics) was added to develop color while protecting the plate from light. Fluorescence was measured by CytoFlour II (PerSeptive).

Selection of Hybridomas

An IMDM medium supplemented with 15% FCS and 10% HCF (hybridoma cloning factor, Origen) was added to the wells showing positive reaction in the abovementioned antibody titer measurement ($1\times10^5$ cells/mL), the resultant suspension was dispensed onto a 96-well culture plate to make the cell concentration about 200 cells/well, and the incubation was carried out at 37° C. in a 5% $CO_2$ incubator. Then, the antibody titer measurement was carried out in the same manner as mentioned above to select hybridomas having high antibody productivity.

Further, limiting dilution was carried out with an IMDM medium supplemented with 15% FCS and 10% HCF to make the selected hybridoma concentration 0.5 to 1 cell/well and the incubation was carried out at 37° C. in a 5% $CO_2$ incubator for about 3 to 4 days, after which the antibody titer was measured in the same manner as described above to select hybridomas having high antibody productivity. Further, the limiting dilution was further repeated to obtain 38 hybridomas producing anti-H1 monoclonal antibody. From these hybridomas, 10 hybridomas showing higher antibody titer than the control antiserum were selected and designated 1F5, 3F2, 15A11, 15F11, 16D1, 16G9, 17C2, 17E2, 21E3, and 22A12.

Test Example 1: Test for Evaluating MLR Suppressing Activity by Culture Supernatant Containing Anti-Histone H1 Monoclonal Antibody Preparation of Culture Supernatant Containing Anti-Histone H1 Monoclonal Antibody Each hybridoma was cultured using an IMDM medium supplemented with 15% FCS and 10% HSF ($1\times10^6$ cells/mL). Using CENTRIPREP YM-10 (MILLIPORE), 15 mL of this culture supernatant was centrifuged (2000 g, 2.5 hours) to obtain a culture supernatant concentrate containing anti-histone H1 monoclonal antibody.

MLR

Using the culture supernatant concentrate obtained (a 1000-fold diluted solution), the MLR suppressing activity evaluation test was carried out in the same manner as in Reference Example 1. As controls, rat serum before immunization (1000-fold diluted solution), rabbit IgG (normal rabbit IgG, 1.6 mg, Santa Cruz Biotechnology) at 1.6 µg/well, anti-histone H1 polyclonal IgG (200 µg, Santa Cruz Biotechnology) at 1.6 µg/well, and tacrolimus at 1.6 µg/well were used. An IMDM medium was used for dilution.

Results are shown in FIG. 1. The culture supernatants of 8 hybridomas, 1F5, 3F2, 15A11, 15F11, 16D1, 16G9, 17C2, and 17E2, showed an MLR suppressing activity as equivalent to anti-histone H1 polyclonal antibody and tacrolimus. In FIG. 1, PVG/PVG represents a mixed culture of PVG lymphocytes which lost proliferating ability by mitomycin C stimulation with PVG lymphocytes which were responding cells, and DA/PVG represents a mixed culture of DA lymphocytes which similarly lost proliferating ability with PVG lymphocytes which were responding cells.

Test Example 2: Specification of Recognition Site of Anti-Histone H1 Monoclonal Antibody -1-Preparation of Samples for Masurement Spleen cells were dissected from PVG rats and subjected to cell disruption according to the method of Weissman (Weissman et al., Science 239, 1018-1021, 1988). The spleen cells were centrifuged with 1 mL of PBS (1500 rpm, 5 minutes) and then recovered. These cells were made into suspension using a syringe and an equal volume of 150 mM NaCl solution was added. The resulting cell suspension was centrifuged (300×g, 10 minutes) to obtain the precipitate and supernatant. This precipitate was designated as an insoluble fraction (containing a nuclear fraction) and the supernatant was designated as a soluble fraction containing cell membranes. To the insoluble fraction, a 5-fold volume (v/v) of sample buffer for electrophoresis (25 mL of 0.25 M Tris-HCl (pH 6.8), 2.0 g of SDS, 9 mL of ultra-pure water, 10 mL of glycerol, 5 mg of BPB) was added. The resulting admixture was boiled for 5 minutes and then centrifuged to obtain a supernatant for use as a sample for measurement. Further, to the soluble fraction containing cell membranes, EDTA was added at a final concentration of 5 mM. Of this soluble fraction containing cell membranes, an aliquot of 100-200 µL was recovered. The remaining soluble fraction containing cell membranes was subjected to ultracentrifugation (4° C., 200000×g, 45 minutes). The resulting precipitate was designated as a cell membrane fraction and the resulting supernatant was designated as a cell membrane-free soluble fraction. The cell membrane fraction was boiled for 5 minutes with a 5-fold volume (v/v) of sample buffer for electrophoresis, and then centrifugation was carried out. The supernatant thus obtained was used as a sample for measurement.

Further, 10 mL of the culture supernatant containing anti-histone H1 monoclonal antibody obtained in Test Example 1 was diluted with a binding buffer (20 mM phosphate buffer, pH 7.4) to obtain 50 mL of a solution. This solution was loaded onto a HiTrap Protein G column (HiTrap Protein G HP, Amersham Biosciences) at a flow rate of 0.2-1 mL/min and circulated at 4° C. for 24 hours. Then, 5 mL of binding buffer was passed through at a flow rate of 1 to 2 mL/min to wash the column. After washing the column, the abovementioned soluble fraction solution containing cell membranes was loaded at a flow rate of 0.2 to 1 mL/min and circulated at 4° C. for 24 hours. Next, 2 mL of binding buffer was passed through at a flow rate of 1 to 2 mL/min to obtain a flow-through fraction. This flow-through fraction was used as a sample for measurement.

Purification of Anti-Histone H1 Monoclonal Antibody 1 mM HCl solution was loaded onto a HiTrap NHS column (HiTrap NHS-activated HP, Amersham Biosciences AB) at a flow rate of 1 tp 2 mL/min and then 1 mL of a histone H1 solution (10.5 mg of histone H1 (Roche Diagnostics), coupling buffer (0.2 M $NaHCO_3$, 0.5 M NaCl, pH-8.3)) was loaded at a flow rate of 1 mL/min, after which the column was immediately sealed to carry out coupling (15 to 30 minutes). After coupling, the inside of the column was washed with buffer A (0.5 M monoethanolamine, 0.5 M NaCl, pH 8.3), buffer B (0.1 M sodium acetate, 0.5 M NaCl, pH 4.0), and neutral buffer (1.0 M Tris-HCl, pH 9.0). Next, the culture supernatant containing anti-histone H1 monoclonal antibody obtained in Test Example 1 was loaded onto the column at a flow rate of 1 mL/min and circulated (4° C., overnight). Next, after washing the column with 5 mL of phosphate buffer, 5 mL of elusion buffer was passed through at a flow rate of 0.2 to 1 mL/min and a purified anti-histone H1 monoclonal antibody was obtained from the eluted fraction.

SDS-PAGE

According to electrophoresis in the discontinuous buffer system by Laemmli (Nature, 227, 680-685, 1970), each sample for measurement was treated by SDS-PAGE. As a control, histone H1 (5 mg, Roche Diagnostics) was used. After SDS-PAGE, the resulting gel was subjected to the following Coomassie staining or Western blotting.

Coomassie Staining

The gel after SDS-PAGE was immersed in a staining solution (0.25% Coomassie brilliant blue R/ethanol:acetic acid: distilled water=9:2:9) and shaken for about one hour, after which the gel was immersed in a destaining solution (ethanol: acetic acid:distilled water=25:8:65) for about one hour for destaining. Then, the gel was immersed in a preservation solution (methanol:acetic acid:distilled water=10:15:175) to destain background.

Western Blotting

Proteins on the gel after SDS-PAGE were transferred onto a PVDF membrane using a semidry-type transferring apparatus (AE-6675, ATTO). Next, the PVDF membrane after the transfer was immersed in a blocking solution (5% skim milk and 1% BSA in a PBST solution) and shaken (at 4° C. for 24 hours or at room temperature for one hour). Next, a solution containing purified anti-histone H1 monoclonal antibody (diluted 500 times with a blocking solution) was added to the PVDF membrane as a primary antibody and after shaking at room temperature for one hour, the membrane was washed with PBST once for 15 minutes and 3 times for 5 minutes. After washing, a secondary antibody (HRP-anti-mouse IgG, Sigma) solution diluted 20000 times with a blocking solution was added to the PVDF membrane and the membrane was shaken at room temperature for one hour. After shaking, the membrane was washed with PBST once for 15 minutes and 3 times for 5 minutes. Further, binding of specific antibodies was detected using an ECL Plus Western blotting detection system (Amersham Biosciences AB) and developed after exposure to light using the X-ray film RX-U (FUJI PHOTO FILM, Tokyo, Japan).

As a result of Western blotting, a specific band was detected at a position of 31 kD of the cell membrane fraction. This band was detected at the same position as histone H1 in Coomassie staining.

Test Example 3: Specification of Recognition Site of Anti-Histone H1 Monoclonal Antibody -2-

The PVG rat spleen cells were suspended in a PBS solution containing 4% formalin and fixed at room temperature for 20 minutes. Further, the spleen cells were washed 3 times with a staining buffer (a PBS solution containing 1% (v/v) FCS and 0.1% (w/v) sodium azide, 4° C.), after which a mixed solution containing $2 \times 10^6$ cells in 100 ml of staining buffer was prepared. To this mixed solution, a primary antibody (2 mL of biotin-labeled anti-histone H1 monoclonal antibody or 5 mL of biotin-labeled normal mouse IgG) was added and the reaction was carried out at 37° C. for one hour. After this reaction, the spleen cells were washed with a staining buffer (4° C.) 3 times, further 100 mL of staining buffer and 1 mL of FITC-labeled streptavidin (BD PharMingen) were added to the spleen cells and the reaction was carried out at room temperature for 30 hours. After the reaction, the spleen cells were washed 3 times with staining buffer (4° C.), and 500 mL of PBS was added to the spleen cells to prepare a suspension. Further, propidium iodide (Sigma) was added to this suspension at a final concentration of 5 mg/mL and the reaction was carried out at room temperature for 20 minutes. The cells thus obtained were sealed with a PBS solution containing 50% glycerin and then examined under a fluorescent microscope.

As a result, only the peripheral part (cell membrane) of the spleen cells was specifically fluorescence-stained.

Test Example 4: Specification of Recognition Site of Anti-Histone H1 Monoclonal Antibody -3-Phage Display For the anti-histone H1 antibody produced by hybridoma 1F5, 3F2, 15F11, 17C2 or 16G9, a panning experiment was carried out using the Ph.D.-12 phage display peptide library kit (purchased from New England BioLabs, Inc.). Each purified monoclonal antibody dissolved in a 0.1 M NaHCO$_3$ solution (pH 8.6) was used for direct coating onto a microtiter plate (Nunc, catalog #430341) and the plate was incubated at 4° C. overnight. Blocking buffer (0.1 M NaHCO3, 5 mg/mL BSA, 0.02% NaN$_3$) was added to each well and the plate was incubated at 4° C. for at least one hour and then washed with TBST (50 mM Tris, 150 mM NaCl, 0.1% Tween 20). In the first panning, $4 \times 10^{10}$ phages in the original library were used for screening. Unbound phages were removed by repetitive washing with TBTS. Bound phages were eluted with 0.2 M glycine-HCl buffer (pH 2.2, 1 mg/mL BSA). The phages eluted were proliferated in 20 mL of *E. coli* ER2738 culture. The resulting phages were precipitated using polyethylene glycol and used for the second panning. Further, the third panning was carried out according to the same procedure. Plaques obtained in the third panning were diluted 100 times and were proliferated using ER2738 culture. Tubes containing the resulting product were incubated with shaking at 37° C. for 4.5 to 5 hours. A single-stranded phage DNA was precipitated and purified using iodide buffer (10 mM Tris-HCl, 1 mM EDTA, 4 M NaI) and ethanol. The phage DNA was dissolved in 20 µl of TE buffer (10 mM Tris-HCl, pH 8.0, 1 mM EDTA) for DNA sequence analysis.

DNA Sequence Analysis

For the purified phage DNA obtained, sequencing PCR reaction was carried out using primer DNA attached to the abovementioned Ph.D.-12 phage display peptide library kit and the DYEnamic™ ET Terminator Cycle Sequencing Premix Kit (Amersham Biosciences) (PCR reaction conditions: 30 cycles consisting of 30 seconds at 95° C., 15 seconds at 50° C., and one minute at 60° C.). The PCR products were purified using the AutoSeq™ G-50 (Amersham Biosciences). Further, the DNA sequence of each of the phage peptide was determined using the ABI PRISM™ 310 Genetic Analyzer (PE Biosystems). Amino acid sequences based on the determined DNA sequences are as follows:

| Hybridoma strain | Amino acid sequence | |
|---|---|---|
| 1F5 | NYQTYTPRPPHS | (SEQ ID NO: 4) |
| 3F2 | VTNNQTSPRWEI | (SEQ ID NO: 5) |
| 15F11 | WKPVSLTLHTHP | (SEQ ID NO: 6) |
| 17C2 | HATGTHGLSLSH | (SEQ ID NO: 7) |
| 16G9 | SSVLYGGPPSAA | (SEQ ID NO: 8) |

Competition ELISA

Each peptide having the amino acid sequence determined from the abovementioned phage DNA was synthesized according to an ordinary method. Competition ELISA was performed using the peptides obtained, each purified monoclonal antibody, and histone H1 antigen (Roche, catalog #1004875). Here, an EZ-Link Sulfo-NHS-Biotinylation kit (Pierce) was used for biotinylation of histone H1 antigen and an ABTS solution (Sigma, A3219) was used as a color forming reagent. Color formation was detected at 405 nm using an ELISA measuring apparatus (Thermo Labsystems, Multiskan Ascent). Measurements were made 3 times to obtain the average of absorption values.

As a result, the abovementioned synthetic peptides were confirmed to inhibit the binding between each purified monoclonal antibody and histone H1 antigen.

The invention claimed is:

1. A purified polypeptide that binds specifically to an anti-histone H1 antibody, consisting of an amino acid sequence represented by SEQ ID NO: 8.

2. A pharmaceutical composition comprising the polypeptide according to claim 1 with a pharmaceutically acceptable carrier.

3. A method for the prediction or diagnosis of transplant rejection in a mammal, comprising measuring the level of immunoreactivity between anti-histone H1 antibody in a biological sample derived from said mammal and the polypeptide according to claim 1, wherein the risk of transplant rejection is predicted or diagnosed to be low when the measured level of immunoreactivity is higher than control or threshold values.

4. The method for the prediction or diagnosis of transplant rejection according to claim 3, wherein said transplant rejection occurs after withdrawal of the administration of an immunosuppressive agent.

* * * * *

SEQUENCE LISTING

<160> NUMBER OF SEQ ID NOS: 8

<210> SEQ ID NO 1
<211> LENGTH: 50
<212> TYPE: PRT
<213> ORGANISM: Homo sapiens
<220> FEATURE:
<223> OTHER INFORMATION: Histone H1 partial sequence

<400> SEQUENCE: 1

Ser Glu Thr Ala Pro Ala Ala Pro Ala Ala Pro Ala Pro Ala Glu Lys
1               5                   10                  15

Thr Pro Val Lys Lys Lys Ala Arg Lys Ser Ala Gly Ala Ala Lys Arg
            20                  25                  30

Lys Ala Ser Gly Pro Pro Val Ser Glu Leu Ile Thr Lys Ala Val Ala
        35                  40                  45

Ala Ser
    50

<210> SEQ ID NO 2
<211> LENGTH: 105
<212> TYPE: PRT
<213> ORGANISM: Bos taurus
<220> FEATURE:
<223> OTHER INFORMATION: Histone H1 partial sequence

<400> SEQUENCE: 2

Ser Glu Thr Ala Pro Ala Ala Pro Ala Ala Pro Pro Ala Glu Lys
1               5                   10                  15

Thr Pro Val Lys Lys Lys Ala Ala Lys Lys Pro Ala Gly Ala Arg Arg
            20                  25                  30

Lys Ala Ser Gly Pro Pro Val Ser Glu Leu Ile Thr Lys Ala Val Ala
        35                  40                  45

Ala Ser Lys Glu Arg Ser Gly Val Ser Leu Ala Ala Leu Lys Lys Ala
    50                  55                  60

Leu Ala Ala Ala Gly Tyr Asp Val Glu Lys Asn Asn Ser Arg Ile Lys
65                  70                  75                  80

Leu Gly Leu Lys Ser Leu Val Ser Lys Gly Thr Leu Val Gln Thr Lys
                85                  90                  95

Gly Thr Gly Ala Ser Gly Ser Phe Lys
            100                 105

<210> SEQ ID NO 3
<211> LENGTH: 221
<212> TYPE: PRT
<213> ORGANISM: Mus musculus
<220> FEATURE:
<223> OTHER INFORMATION: Histone H1 partial sequence

<400> SEQUENCE: 3

Met Ser Glu Thr Ala Pro Ala Ala Pro Ala Ala Pro Ala Pro Val Glu
1               5                   10                  15

Lys Thr Pro Val Lys Lys Lys Ala Lys Lys Thr Gly Ala Ala Ala Gly
            20                  25                  30

Lys Arg Lys Ala Ser Gly Pro Pro Val Ser Glu Leu Ile Thr Lys Ala
        35                  40                  45

Val Ala Ala Ser Lys Glu Arg Ser Gly Val Ser Leu Ala Ala Leu Lys
    50                  55                  60

Lys Ala Leu Ala Ala Ala Gly Tyr Asp Val Glu Lys Asn Asn Ser Arg

```
                65                  70                  75                  80
Ile Lys Leu Gly Leu Lys Ser Leu Val Ser Lys Gly Thr Leu Val Gln
                        85                  90                  95
Thr Lys Gly Thr Gly Ala Ser Gly Ser Phe Lys Leu Asn Lys Lys Ala
                100                 105                 110
Ala Ser Gly Glu Ala Lys Pro Lys Ala Lys Lys Ala Gly Ala Ala Lys
            115                 120                 125
Ala Lys Lys Pro Ala Gly Ala Ala Lys Lys Pro Lys Lys Ala Thr Gly
        130                 135                 140
Ala Ala Thr Pro Lys Lys Thr Ala Lys Lys Thr Pro Lys Lys Ala Lys
145                 150                 155                 160
Lys Pro Ala Ala Ala Ala Gly Ala Lys Lys Val Ser Lys Ser Pro Lys
                165                 170                 175
Lys Val Lys Ala Ala Lys Pro Lys Lys Ala Ala Lys Ser Pro Ala Lys
                180                 185                 190
Ala Lys Ala Pro Lys Ala Lys Ala Ser Lys Pro Lys Ala Ser Lys Pro
            195                 200                 205
Lys Ala Thr Lys Ala Lys Lys Ala Ala Pro Arg Lys Lys
    210                 215                 220

<210> SEQ ID NO 4
<211> LENGTH: 12
<212> TYPE: PRT
<213> ORGANISM: Artificial
<220> FEATURE:
<223> OTHER INFORMATION: Synthetic peptide

<400> SEQUENCE: 4

Asn Tyr Gln Thr Tyr Thr Pro Arg Pro Pro His Ser
1               5                   10

<210> SEQ ID NO 5
<211> LENGTH: 12
<212> TYPE: PRT
<213> ORGANISM: Artificial
<220> FEATURE:
<223> OTHER INFORMATION: Synthetic peptide

<400> SEQUENCE: 5

Val Thr Asn Asn Gln Thr Ser Pro Arg Trp Glu Ile
1               5                   10

<210> SEQ ID NO 6
<211> LENGTH: 12
<212> TYPE: PRT
<213> ORGANISM: Artificial
<220> FEATURE:
<223> OTHER INFORMATION: Synthetic peptide

<400> SEQUENCE: 6

Trp Lys Pro Val Ser Leu Thr Leu His Thr His Pro
1               5                   10

<210> SEQ ID NO 7
<211> LENGTH: 12
<212> TYPE: PRT
<213> ORGANISM: Artificial
<220> FEATURE:
<223> OTHER INFORMATION: Synthetic peptide

<400> SEQUENCE: 7

His Ala Thr Gly Thr His Gly Leu Ser Leu Ser His
1               5                   10
```

```
<210> SEQ ID NO 8
<211> LENGTH: 12
<212> TYPE: PRT
<213> ORGANISM: Artificial
<220> FEATURE:
<223> OTHER INFORMATION: Synthetic peptide

<400> SEQUENCE: 8

Ser Ser Val Leu Tyr Gly Gly Pro Pro Ser Ala Ala
1               5                   10
```